| United States Patent [19] | [11] Patent Number: 4,568,667 |
| --- | --- |
| Shirakawa et al. | [45] Date of Patent: Feb. 4, 1986 |

[54] AQUEOUS PREPARATION CONTAINING VITAMIN E AND SAPONINS

[75] Inventors: Yoichi Shirakawa; Makoto Itoh; Keigi Koyama; Yoshio Minowa, all of Tokyo, Japan

[73] Assignees: Eisai Company, Ltd.; Asahi Denka Kogyo Kabushiki Kaisha, both of Tokyo, Japan

[21] Appl. No.: 530,735

[22] Filed: Sep. 9, 1983

[30] Foreign Application Priority Data

Sep. 10, 1982 [JP] Japan .................................. 57-157875

[51] Int. Cl.$^4$ ............................................. C07J 17/00
[52] U.S. Cl. ........................................ 514/26; 514/53; 514/54; 514/58; 514/60
[58] Field of Search ................ 424/182; 536/5, 6, 6.1, 536/6.2, 6.3; 514/26, 53, 54, 58, 60

[56] References Cited

U.S. PATENT DOCUMENTS

| 3,839,317 | 10/1974 | Higuchi | 424/182 |
| 4,254,111 | 3/1981 | Pegel et al. | 536/5 |
| 4,457,918 | 7/1984 | Holick et al. | 536/4.1 |

*Primary Examiner*—Johnnie R. Brown
*Attorney, Agent, or Firm*—Birch, Stewart, Kolasch & Birch

[57] ABSTRACT

An aqueous preparation containing vitamin E prepared by emulsifying or solubilizing vitamin E in an aqueous phase in the presence of a saponin shows excellent transparency and thermal stability, and can be widely used in the fields of medicines, cosmetics, foodstuffs, animal feeds and the like. Quillaiasaponin is the preferred saponin.

10 Claims, No Drawings

AQUEOUS PREPARATION CONTAINING VITAMIN E AND SAPONINS

BACKGROUND OF THE INVENTION (1) Field of the Invention

This invention relates to an aqueous preparation containing vitamin E.

(2) Description of the Prior Art

Vitamin E has been widely used as a vitamin or as an anti-oxidant in the fields of medicines, cosmetics, foodstuffs and the like. Since it is an oil-soluble compound, vitamin E is easily solubilized in oil or fat without trouble to give a desired product. However in case that one intends to make an aqueous preparation containing vitamin E, there exist various problems to be solved.

In preparing an aqueous preparation containing vitamin E in the field of medicines, it is possible to solubilize it with nonionic surfactants or solubilizing aids. However in the field of foodstuffs, the use of these surfactants is not permitted. Further the above mentioned aqueous preparation obtained in the field of medicines has some problems to be solved, such as deterioration during heat sterilization or with the passage of time.

SUMMARY OF THE INVENTION

We have made a study on water-solubilization of vitamin E using a number of natural surfactants excluding the conventionally employed surfactants, and as a result, have found that a saponin such as quillasaponin remarkably solubilizes vitamin E.

Aqueous preparations containing vitamin E according to the present invention are characterized in that vitamin E is emulsifed or solubilized in an aqueous phase in the presence of a saponin.

DESCRIPTION OF THE PREFERRED EMBODIMENTS

Quillaiasaponin has been known as a foaming agent for non-alcoholic refreshing drinks such as cola drinks and root beer. However its ability for solubilizing vitamin E has been unknown so far.

In the present invention, any synthetic or natural vitamin E products can be used as vitamin E. It is preferable that the product contain d-α-tocopherol having an effect like vitamin E. Those obtained by the extraction of natural materials usually contain oils and fats. In making an aqueous preparation in accordance with the present invention, it is preferable that such preparations contain 40% or more of tocopherol. The coexistence in vitamin E of oil-soluble compounds (except for triglycerides) having pharmacological effects is allowable. The examples of these oil-soluble compounds are lecithin, the vitamin Ks, vitamin A, vitamin D, ubiquinone, etc.

As the saponin used in the present invention, there are listed those derived from various plants such as quillaiasaponin, soybean saponin, tea saponin, among which quillaiasaponin is especially preferred.

According to the present invention, the stability of aqueous preparations containing vitamin E is further improved by using together with the saponin the following compounds, for example, surfactants such as fatty acid monoglycerides, polyglycerin fatty acid esters and sucrose fatty acid esters and/or ethylene glycol, diethylene glycol, triethylene glycol or higher polyethylene glycols; propylene glycol, dipropylene glycol or higher polypropylene glycols; glycerin, diglycerin or higher polyglycerins; sugar-alcohols such as sorbitol, mannitol, xylitol or multitol; monosaccharides, disaccharides or trisaccharides such as glucose, lactose, sucrose, maltose, galactose; various invert sugars obtained by hydrolysis of starches; starch syrup; dextrin; isomerized sugars; syrups; honey; and polyhydroxyl compounds such as those prepared by reacting the above mentioned various compounds with alkylene oxide such as ethylene oxide or propylene oxide.

In order to improve the thermal stability and dilution of an aqueous preparation containing vitamin E, it is preferable to use a monoglyceride of a fatty acid having from 6 to 12 carbon atoms. The dilution stability used herein means the stability when the aqueous preparation is diluted with an aqueous medium whose pH is in the acidic region. Further, the above mentioned stabilities are drastically improved by using a polyglycerin fatty acid ester.

When a considerable amount of oils and fats such as triglycerides are included in a tocopherol-containing oil, only tocopherol can be solubilized, but the oils and fats are retained as nondissolved materials, resulting in difficulty of obtaining a uniform aqueous preparation. In this case, use of sanctioned surfactants fairly contributes to the stabilization of the aqueous preparation. However the problems originating in the nature of the surfactant, such as decrease in thermal stability, pH stability, dilution stability and so on may be caused depending on the amount of the surfactant used. Therefore in case that a surfactant is used, attention should be paid to the amount thereof.

The amount of the saponin used for water-solubilization of vitamin E is from 0.3 to 10 times (by weight), preferably from 0.5 to 4 times, with respect to the amount of vitamin E. The amount of the saponin may be reduced by the addition of a surfactant usable with the saponin.

When the monoglyceride of a fatty acid having from 6 to 12 carbon atoms and/or a polyglycerin fatty acid ester are used together with the saponin, their amounts are from 0.01 to 0.5 times, respectively, with respect to the vitamin E.

The aqueous preparations of the present invention may contain sugars, organic acids, amino acids, etc. in an amount that they do not disturb the effect of the saponin.

The aqueous preparations of the present invention can be prepared in various manners. Most simply, vitamin E is added dropwise to an aqueous solution containing 0.1–40%, preferably 1–30% of saponin under stirring to give a uniform aqueous preparation containing vitamin E. Warming hastens solubilization. If a sufficient amount of saponin is present, solubilization can finally be attained by any mixing method.

The concentration of vitamin E in the aqueous preparation of the present invention varies from 0.001 to about 15% depending on the factors such as the above mentioned saponin concentration of the aqueous solution. Aqueous preparations containing from 1 to 10% of vitamin E are preferably used for various applications. Practically, an aqueous preparation containing a high concentration of vitamin E is first obtained, and the concentrated preparation obtained above is diluted upon use.

The aqueous preparation containing vitamin E of the present invention can be used as it is or after being diluted with water. It is uniformly applied to foodstuffs, medicines, cosmetics, animal feeds or the like, in various ways such as addition by means of mixing, impregnation by means of immersion and surface coating or supporting by means of coating or spraying. In the above mentioned manners, there are obtained vitamin E-enriched products and highly oxidation-resistant products. The appearance and quality of these products are not impaired because vitamin E is dispensed in a ultra-fine particle form throughout the product.

The aqueous preparations containing vitamin E of the present invention can be powdered by available means using excipients, and can be used in the powdered form.

According to the present invention, it becomes possible to use vitamin E in a substantially transparent form in an aqueous solution. Such water-solubilization of vitamin E greatly contributes to expansion of applications of vitamin E in the fields of foodstuffs, medicines, cosmetics, animal feeds or the like. Especially when added to table luxuries such as coffee or cocoa, the aqueous preparation of the present invention prevents them from losing their flavor due to heating. The aqueous preparation of the present invention is also effective when added to fruit juices or nutrition drinks.

The invention will be more clearly understood with reference to the following examples. However, this invention should not be limited to the examples.

EXAMPLE 1

Five grams of natural tocopherol (available from Japan Chemical Animal-Feed Co., Ltd. and containing a total tocopherol content of 90%) was added to 95 g of an aqueous solution containing 15 g of quillaiasaponin while stirring it with a magnetic stirrer. Stirring was continued until turbidity disappeared. A yellowish brown transparent solution was obtained. When diluted with water 10, 100 and 1000 times, the resulting solutions were substantially transparent although the color tone was changed.

EXAMPLE 2

To 5 g of E mix-80 (available from Eisai Co., Ltd. and containing 80% of tocopherol homologues and 20% of soybean oil) was added 0.3 g of Poem M-100 (monoglyceride of fatty acid having 8 carbon atoms available from Riken Vitamin Co.). After being uniformly mixed, the mixture was poured into a solution containing 30 g of 75% starch syrup, 9 g of quillaiasaponin and 56 g of water while stirring it with a glass rod. As the result, a transparent yellowish red solution was obtained. The 500 times dilution of the solution with water gave a faintly bluish transparent solution. No noticeable change was observed after the pH value thereof is altered to 4 by adding citric acid. Similarly no noticeable change was observed after the aqueous solution is heated at 95° C. for 30 min. and thereafter cooled to room temperature.

EXAMPLE 3

To an aqueous solution comprising 140 g of 75% starch syrup, 20 g of quillaiasaponin, and 216 g of water was added, under mild stirring with a homomixer, an oily solution obtained by mixing 20 g of E mix-80, 3.2 g of ML-750 (polyglycerin fatty acid ester available from Sakamoto Pharmaceuticals Co., Ltd.) and 0.8 g of Poem M-100. As the result, a transparent yellowish red solution was obtained. In the same manner as in Example 2, the resulting solution was diluted with water to obtain diluted solutions which have excellent transparancy, pH stability and thermal stability like those obtained in Example 2.

EXAMPLE 4

To an aqueous solution comprising 100 g of 75% starch syrup, 15 g of tea saponin and 155 g of water was added, under mild stirring with a homomixer, an oily solution obtained mixing 15 g of E mix-80, 2.3 g of ML-750 and 0.7 g of Poem M-100. As the result, a transparent yellowish red solution was obtained. In the same manner as in Example 2, the resulting solution was diluted with water to obtain diluted solutions which have excellent transparancy, pH stability and thermal stability like those obtained in Example 2.

APPLICATION EXAMPLE

The coffee drinks used are shown in Table 1.

TABLE 1

|  | Coffee Drink | | |
| --- | --- | --- | --- |
|  | 1 (with milk) | 2 | 3 (black) |
| Coffee Extract | 2.6 g | 2.6 g | 4.0 g |
| Sugar | 7.0 g | 9.3 g | 9.3 g |
| Flavor | 0.01 ml | 0.01 ml | 0.1 ml |
| Milk | 4.5 g | 4.5 g | 0 g |
| Water | up to 100 g in total | | |

To the coffee drinks shown in Table 1 were added the aqueous containing preparation of Vitamin E of Example 1, the commercially available vitamin E-containing emulsion I (from A Co., Ltd.) and the commercially available vitamin E-containing emulsion II (from B Co., Ltd.), respectively, so that the amount of vitamin E contained becomes 0.0018 g/dl. Each mixture was heat-treated in an autoclave at 120° C. for 1 hour.

Organoleptic evaluation was made in five grades by five panelists. Non-heated coffee drinks to which no vitamin E-containing emulsion is added are employed as the control. The results are shown in Table 2.

TABLE 2

|  |  | Organoleptic Evaluation | | | | |
| --- | --- | --- | --- | --- | --- | --- |
|  | pH | *1 | *2 | *3 | *4 | remarks |
| coffee drink No. 1 of Table 1 | | | | | | |
| (a) | 6.73 | 4.0 | 3.7 | 3.7 | 3.7 | |
| (b) | 6.70 | 4.0 | 3.9 | 4.0 | 3.9 | excellent natural feeling |
| (c) | 6.72 | 3.8 | 2.3 | 2.3 | 2.3 | odd flavor* |
| (d) | 6.72 | 3.8 | 3.5 | 3.4 | 3.4 | |
| coffee drink No. 2 of Table 1 | | | | | | |
| (a) | 5.59 | 3.9 | 2.8 | 3.2 | 3.0 | |
| (b) | 5.59 | 4.2 | 2.8 | 3.3 | 3.2 | excellent natural feeling |
| (c) | 5.55 | 3.2 | 2.0 | 2.0 | 2.0 | slightly odd flavor* |
| (d) | 5.51 | 4.0 | 2.8 | 2.8 | 3.0 | |
| coffee drink No. 3 of Table 1 | | | | | | |
| (a) | 4.47 | 4.5 | 3.5 | 3.8 | 3.6 | |
| (b) | 4.47 | 4.6 | 3.6 | 4.0 | 3.9 | retained more natural feeling |
| (c) | 4.46 | 3.7 | 1.7 | 1.3 | 1.3 | odd flavor* medicine-smell, became cloudy |
| (d) | 4.45 | 3.6 | 2.1 | 1.7 | 2.1 | slightly stronger acid taste, lost the characteristics of coffee, |

TABLE 2-continued

| | Organoleptic Evaluation | | | | |
|---|---|---|---|---|---|
| pH | *1 | *2 | *3 | *4 | remarks |
| | | | | | became cloudy |

Note:
(a) control (without vitamin E emulsion)
(b) with the aqueous perparation of Example 1
(c) with the emulsion I from A Co., Ltd.
(d) with the emulsion II from B Co., Ltd.
*1 aroma
*2 taste or flavor
*3 natural feeling
*4 total evaluation
*odd flavor means flavor like spoiled oranges.

What is claimed is:

1. An aqueous preparation containing vitamin E wherein the vitamin E is emulsified or solubilized in the aqueous phase in the presence of a saponin selected from the group consisting of quillaiasaponin, soybean saponin and tea saponin, the amount of the saponin in said preparation being from 0.3 to 10 times by weight with respect to the amount of vitamin E.

2. An aqueous preparation containing vitamin E according to claim 1, wherein the saponin is quillaiasaponin.

3. An aqueous preparation containing vitamin E according to claim 1, further including a fatty acid monoglyceride, the amount of the fatty acid monoglyceride being from 0.01 to 0.5 times by weight with respect to the amount of vitamin E.

4. An aqueous preparation containing vitamin E according to claim 3, wherein the fatty acid constituting said fatty acid monoglyceride has from 6 to 12 carbon atoms.

5. An aqueous preparation containing vitamin E according to claim 1, further including polyglycerin fatty acid ester, the amount of the polyglycerin fatty acid ester being from 0.01 to 0.5 times by weight with respect to the amount of vitamin E.

6. An aqueous preparation containing vitamin E according to claim 1, further including a polyhydroxyl compound selected from the group consisting of ethylene glycol, diethylene glycol, triethylene glycol, higher polyethylene glycols, propylene glycol, dipropylene glycol, higher polypropylene glycols, glycerin, diglycerin, higher polyglycerins, sugar-alcohols, disaccharides, trisaccharides, invert sugars, starch syrup, dextrin, isomerized sugars, syrups and honey.

7. An aqueous preparation containing vitamin E according to claim 6, wherein the polyhydroxyl compound is starch syrup.

8. An aqueous preparation containing vitamin E according to claim 2, further including a fatty acid monoglyceride together with the saponin.

9. An aqueous preparation containing vitamin E according to claim 8, wherein the fatty acid constituting said fatty acid monoglyceride has from 6 to 12 carbon atoms.

10. An aqueous preparation containing vitamin E according to claim 1, wherein the amount of saponin in said preparation is from 0.5 to 4 times by weight with respect to the amount of vitamin E.

* * * * *